(12) United States Patent     (10) Patent No.:   US 12,605,226 B2

Näslund     (45) Date of Patent:     Apr. 21, 2026

(54) RADIATION THERAPY REFERENCE POSITIONING MARKER

(71) Applicant: Camtomsam AB, Huddinge (SE)

(72) Inventor: Ingemar Näslund, Huddinge (SE)

(73) Assignee: CAMTOMSAM AB, Huddinge (SE)

( * ) Notice: Subject to any disclaimer, the term of this patent is extended or adjusted under 35 U.S.C. 154(b) by 82 days.

(21) Appl. No.: 18/040,210

(22) PCT Filed: Oct. 6, 2021

(86) PCT No.: PCT/SE2021/050980

§ 371 (c)(1),
(2) Date: Feb. 1, 2023

(87) PCT Pub. No.: WO2022/075911

PCT Pub. Date: Apr. 14, 2022

(65) Prior Publication Data

US 2023/0285109 A1    Sep. 14, 2023

(30) Foreign Application Priority Data

Oct. 7, 2020    (SE) .................................... 2051174-7

(51) Int. Cl.
*A61B 90/00*       (2016.01)
(52) U.S. Cl.
CPC ...... *A61B 90/39* (2016.02); *A61B 2090/3925* (2016.02); *A61B 2090/3954* (2016.02)
(58) Field of Classification Search
CPC .... A61B 2090/3908; A61B 2090/3925; A61B 2090/3954; A61B 2090/3966;

(Continued)

(56) References Cited

U.S. PATENT DOCUMENTS

| | | | |
|---|---|---|---|
| 9,579,160 | B2 | 2/2017 | Näslund |
| 2003/0088144 | A1 | 5/2003 | Terwilliger et al. |

(Continued)

FOREIGN PATENT DOCUMENTS

| | | |
|---|---|---|
| JP | 2008504865 A | 2/2008 |
| JP | 2014519375 A | 8/2014 |

(Continued)

OTHER PUBLICATIONS

International Search Report and Written Opinion of corresponding Application No. PCT/SE2021/050980 dated Dec. 23, 2021.

(Continued)

*Primary Examiner* — Brooke Lyn Klein
(74) *Attorney, Agent, or Firm* — Renner, Otto, Boisselle & Sklar, LLP

(57) ABSTRACT

The present invention relates to a radiation therapy or microwave therapy or cryosurgery or ultrasound therapy reference positioning marker (5) adapted to be implanted in tissue using a hollow injection needle (4), wherein the marker comprises an elongated object with a longitudinal axis (CL) and have cross-sections (A-A, B-B, C-C, D-D, E-E, F-F) of the object, perpendicular to said longitudinal axis (CL), being adapted to fit within an inner diameter (DI) of the needle (4), wherein the marker (5) comprises a plurality of first segments (1) having a first cross-section and one or more second segments (2) having a second set of cross-sections, wherein an area of the first cross-section is selected relatively larger than area/s of the second set of cross-sections, and wherein the first segments (1) and second segments (2) are arranged alternately after each other along the longitudinal axis (CL), wherein the one or more of second segments (2) are provided with one or more deformation segments (22) adapted to ensure that any deformation of the plurality of second segments, when positioned (Continued)

inside the needle, occurs in a predetermined location/s between adjoining first segments, such that the plurality of first segments remain linearly aligned in the injection needle when it encounters resistance during implantation into the tissue.

8 Claims, 10 Drawing Sheets

(58) Field of Classification Search
CPC ........... A61B 2090/3987; A61B 90/39; A61N 2005/1058; A61N 5/1027; A61N 5/1049
See application file for complete search history.

(56) References Cited

U.S. PATENT DOCUMENTS

| | | | | |
|---|---|---|---|---|
| 2008/0058769 A1* | 3/2008 | Naslund | ................. | A61B 90/39 |
| | | | | 604/529 |
| 2009/0131734 A1* | 5/2009 | Neustadter | ............. | A61B 90/39 |
| | | | | 600/8 |
| 2012/0323117 A1 | 12/2012 | Neustadter et al. | | |
| 2013/0096427 A1 | 4/2013 | Murray et al. | | |
| 2014/0088419 A1* | 3/2014 | Naslund | ................. | A61B 90/39 |
| | | | | 600/431 |
| 2014/0309522 A1 | 10/2014 | Fullerton et al. | | |
| 2015/0045665 A1 | 2/2015 | Lau | | |
| 2016/0303348 A1 | 10/2016 | Leung et al. | | |
| 2017/0143444 A1 | 5/2017 | Naslund | | |

FOREIGN PATENT DOCUMENTS

| | | | |
|---|---|---|---|
| WO | 2007094001 A2 | 8/2007 | |
| WO | 2016193753 A2 | 12/2016 | |

OTHER PUBLICATIONS

Search Report mailed Apr. 15, 2021, for Swedish Application No. 2051174-7.

* cited by examiner

RADIATION THERAPY REFERENCE POSITIONING MARKER

This application is a national phase of International Application No. PCT/SE2021/050980 filed Oct. 6, 2021, which claims priority to Swedish Application No. 2051174-7 filed Oct. 7, 2020, each of which is hereby incorporated herein by reference in its entirety.

TECHNICAL FIELD

The present invention relates to a radiation therapy reference positioning marker, in particular a marker adapted to be implanted in tissue using a hollow needle, and is adapted to be forming an expanded and entangled ball when implanted into tissue.

BACKGROUND

During therapy, e.g., radiation therapy, such as radiation treatment of cancer, treatment of target areas is generally repeated over time. Radiation equipment is generally calibrated for a particular target area using radiation equipment positioning based on imaging systems, such as computer tomography imaging systems. Imaging systems may be combined, and include e.g., X-ray imaging, Magnetic Resonance Imaging, MRI, systems and Positron Emission Tomography, PET, imaging, ultrasound imaging or any other suitable imaging technique. The accuracy of the calibration/positioning of the radiation equipment is of great importance to ensure a good effect of the radiation therapy as well as minimizing the unwanted effects on healthy tissue.

Further applications include guidance during surgery, where a surgeon needs to navigate his tools during a procedure.

To aid in the calibration/positioning of the radiation equipment and/or tools of the surgeon, reference positioning markers implanted in tissue are used. The reference positioning markers typically indicate the position of the target area in a patient body and allows for improved calibration/positioning of the radiation equipment when repeating radiation therapy over time.

A prior art reference positioning marker is disclosed in U.S. Pat. No. 9,579,160 and is adapted to be implanted in tissue using a hollow needle. The reference positioning marker solves some challenges for reference positioning markers, such as facilitating simple implantation in the body, providing sufficient mass to provide good contrast in images generated by different types of imaging systems, minimizing the risk of bleedings and infections and ensuring that the reference positioning marker stays mainly in the same position the body over time.

However, the prior art marker above has the drawback that the reference positioning marker may be deformed in a way that friction to the hollow needle used for implantation of the reference positioning marker is increased, or even causing the reference positioning marker to jam inside the needle.

Thus, there is a need for an improved reference positioning marker.

OBJECTS OF THE INVENTION

An objective of embodiments of the present invention is to provide a solution which mitigates or solves the drawbacks and problems described above.

SUMMARY OF THE INVENTION

The above and further objectives are achieved by the subject matter described herein. Further advantageous implementation forms of the invention are further defined herein According to a first aspect of the invention the objects of the invention is achieved by a radiation therapy reference positioning marker adapted to be implanted in tissue using a hollow injection needle, wherein the marker comprises an elongated object with a longitudinal axis and have cross-sections of the object, perpendicular to said longitudinal axis, being adapted to fit within an inner diameter of the needle, wherein the marker comprises a plurality of first segments having a first cross-section and one or more second segments having a second set of cross-sections, wherein an area of the first cross-section is selected relatively larger than area/s of the second set of cross-sections, and wherein the first segments and second segments are arranged alternately after each other along the longitudinal axis, wherein the one or more of second segments are provided with one or more deformation segments adapted to ensure that any deformation of the plurality of second segments, when positioned inside the needle, occurs in a predetermined location/s between adjoining first segments, such that the plurality of first segments remain linearly aligned in the injection needle when it encounters resistance during implantation into the tissue.

The advantage of the invention according to the first aspect is at least that the risk for deformation in a way that friction is decreased and/or the risk of the reference positioning marker jamming inside the needle is reduced or even eliminated.

In one embodiment of the first aspect of the invention the one or more deformation segments are centered between the respective adjoining first segments and each comprises a minimum area of the areas of the second set of cross-sections.

In one embodiment of the first aspect of the invention the minimum area is further centered around the longitudinal axis.

In one embodiment of the first aspect of the invention the one or more deformation segments are formed as a bend extending from an outer surface of ends of the respective second segment in a direction towards said longitudinal axis.

In one embodiment of the first aspect of the invention the bend has a bending radius equal to or greater than half of a diameter of a circle enclosing an outline of the first cross-section.

In one embodiment of the first aspect of the invention, the one or more deformation segments comprises one single deformation segment which is formed as an elongated element provided with a weakening indentation on a side of the deformation segments facing said longitudinal axis.

In one embodiment of the first aspect of the invention, the one or more deformation segments comprises one single deformation segment which is formed as an elongated element provided with sharp crease, wherein the crease has a direction perpendicular from a cylinder formed by outer surfaces of the first segments towards said longitudinal axis.

In one embodiment of the first aspect of the invention, the plurality of second segments further comprises two anchor segments arranged between either adjoining first segment respectively and the one or more deformation segments, wherein the anchor segments comprise cross-sections ranging from an area equal to the area of a first cross-section at ends of the respective second segment to a reduced area of the one or more deformation segments.

In one embodiment of the first aspect of the invention, the marker comprises a first material with a density of at least 10 g/cm3, and this material constitutes at least 90% by volume of the marker, wherein the marker comprises a second material that is magnetic and that constitute at the most 10% by volume of the marker, and wherein the marker comprises an alloy or granulation mixture comprising the first material and the second material.

In one embodiment of the first aspect of the invention, the marker comprises between two and fifteen first segments and between one and fourteen second segments.

An advantage of the embodiment according to the first aspect is that any deformation of the plurality of second segments, when positioned inside the needle, occurs in a predetermined location/s between adjoining first segments, such that the plurality of first segments remain linearly aligned in the injection needle when it encounters resistance during implantation into the tissue.

Further applications and advantages of embodiments of the invention will be apparent from the following detailed description.

BRIEF DESCRIPTION OF THE DRAWINGS

FIG. 9A-C shows different cross-sections of a first segment according to one or more embodiments of the present disclosure.

Figure 1A:
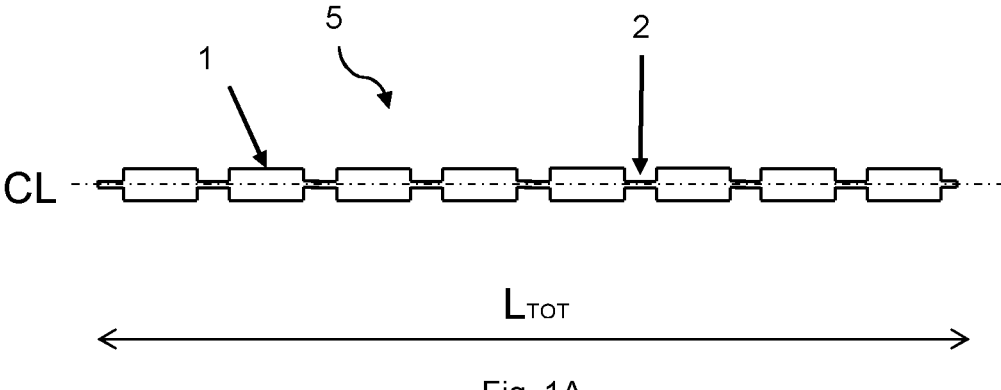
FIG. 1A-C shows a prior art reference positioning marker.

A more complete understanding of embodiments of the invention will be afforded to those skilled in the art, as well as a realization of additional advantages thereof, by a consideration of the following detailed description of one or more embodiments. It should be appreciated that like reference numerals are used to identify like elements illustrated in one or more of the figures.

DETAILED DESCRIPTION

An "or" in this description and the corresponding claims is to be understood as a mathematical OR which covers "and" and "or", and is not to be understand as an XOR (exclusive OR). The indefinite article "a" in this disclosure and claims is not limited to "one" and can also be understood as "one or more", i.e., plural.

In the present disclosure the term "radiation therapy reference positioning marker", herein used interchangeably with the term "marker", denotes an arrangement adapted to aid in the calibration/positioning of the radiation equipment configured to deliver radiation therapy to a target area in tissue of a patient. The reference positioning marker is adapted to be implanted in tissue of a patient (human or animal). The reference positioning marker is adapted to indicate the position of the target area in an image of a patient's body and allows for improved calibration/positioning of the radiation equipment when repeating radiation therapy over time. An example of a radiation therapy reference positioning marker is shown in U.S. Pat. No. 9,579,160.

In the present disclosure discloses a radiation therapy reference positioning marker which adapted to be implanted in tissue using a hollow needle by configuring the marker as an elongated object adapted to fit within an inner diameter of the needle. This facilitates simple implantation in the body.

In the present disclosure, the term "hollow injection needle" and/or "needle" are used interchangeably and denotes, e.g., a hypodermic needle.

In the present disclosure, the term "cross-section" denotes a non-empty intersection of a plane perpendicular to a longitudinal axis of an elongated object or a first segment or a second segment as disclosed herein. In other words, creating cross-sections by cutting an object into slices creates a plurality of parallel cross-sections.

The present disclosure the terms "millimeter" and "mm" are used interchangeably.

The marker is formed by first and second segments arranged alternately after each other along a longitudinal axis, which allows the marker to remain linearly aligned in the injection needle and then to form an entangled and expanding ball of first and second segments when exiting the needle and being implanted in tissue of a patient.

The marker comprises a plurality of first segments having a first cross-section and one or more/plurality of second segments having a second set of cross-sections. An area of the first cross-section is selected relatively larger than area/s of the second set of cross-sections. This facilitates or ensures bending/folding of the marker in the one or more second segments when it encounters resistance during implantation into the tissue.

The present disclosure ensures that any deformation of the plurality of second segments, when positioned inside the needle and subjected to a force along or parallel to the longitudinal axis, occurs in a predetermined location/s between adjoining first segments, such that the plurality of first segments remain linearly aligned along the longitudinal axis in the injection needle when it encounters resistance during implantation into the tissue. This is ensured by providing one or more/plurality of second segments which are each provided with one or more deformation segments adapted to deform in one or more predetermined locations.

In other words, if a force acts along the longitudinal axis, any deformation of the one or more/plurality of second segments occurs are controlled such that the plurality of first segments remain aligned along the longitudinal axis when they are positioned in the injection needle, and still allow the first segments to tilt and/or fold and form an entangled and expanding ball after exiting the needle.

Deformation of the one or more/plurality of second segments are typically controlled by making them weaker than the plurality of first segments, and further by positioning one or more weakest points of each of the one or more/plurality of second segments such that the plurality of first segments remain linearly aligned along the longitudinal axis in the injection needle when it encounters resistance during implantation into the tissue. The one or more deformation segments may be formed using different shapes, such as circle, semi-circle, circle segment, oval, triangle or star, without departing from the present disclosure.

The applications of the reference positioning marker herein include: Use as a breast tissue marker, to guide surgeons when they cut out breast tumors.

Use in image-guided surgery through endoscopes; Use in image-guided robotic surgery.

Use in image-guided High-Intensity Focused Ultrasound (HIFU).

Use in image-guided RadioFrequency Ablation (RFA) and MicroWave Ablation (MWA).

Use in marking the extent of cryoablation.

Use as a biopsy marker (simply marking where the biopsy was taken, for future reference);

The above list is not exhaustive, and further applications are visioned

FIG. 1A shows a side view of a prior art reference positioning marker 5. The marker 5 is formed by first 1 and second 2 segments arranged alternately after each other along a longitudinal axis CL, which allows the marker to remain linearly aligned in the injection needle and then to tilt and/or fold to form an entangled and expanding ball of first and second segments when exiting the needle and being implanted in tissue of a patient. The marker comprises a plurality of first segments 1 having a first cross-section A-A and one or more/plurality of second segments 2 having a second set of cross-sections B-B. An area of the first cross-section A-A is selected relatively larger than area/s of the second set of cross-sections B-B. This facilitates or ensures bending/folding of the marker 5 in the one or more second segments 2 when it encounters resistance during implantation into the tissue, i.e., a force that acts along the longitudinal axis providing resistance when implanting the marker 5. The reference positioning marker 5 has a total length of $L_{TOT}$, e.g., in a range of about 10-30 mm. It is understood that of $L_{TOT}$ may be selected to any suitable length related to a length of the hollow needle used to implant the marker 5. A preferred total length of $L_{TOT}$ is 20 millimeters or in the range of [5-35 millimeters].

Figure 1B:
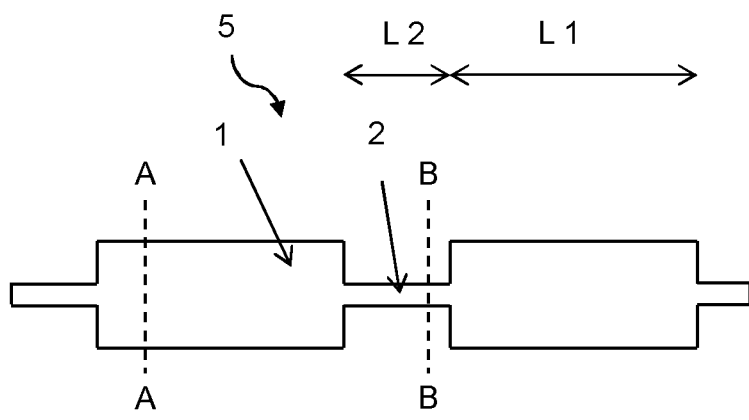

In one example, the marker comprises ten first segments, nine second segments and has a total length of $L_{TOT}$ of 20 millimeters. In one example, the marker comprises fifteen first segments, fourteen second segments and has a total length of $L_{TOT}$ of 30 millimeters. In one further example, the marker comprises two first segments, one second segment and has a total length of $L_{TOT}$ of 3 millimeters FIG. 1B shows a detailed side view of the prior art reference positioning marker 5. As mentioned above, the marker 5 typically comprises a plurality of first segments 1 having a first cross-section A-A and at least one or a plurality of second segments 2 having a second set of cross-sections B-B. The first area AR1 of the first cross-section A-A is selected relatively larger, e.g., ten times, than second area/s AR2 of the second set of cross-sections B-B. In embodiments where circular cross-sections are used, the relation of diameter between the first segments 1 and the second segments 2 may be about 6:1. In other words, the second set of cross-sections B-B typically has a second area AR2 in the range of [1%-10%] of the first area AR1 of the first cross-section A-A.

In one example, the first segments 1 have a diameter that is between 0.2-0.7 millimeters, mm, and the second segments 2 have a diameter B2 that is between 0.025-0.12 mm. In a preferred embodiment, the first segments 1 have a diameter of 0.28 mm, each with a first area AR1 of 0.0615 mm². The second segments have a diameter of 0.05 mm, and each has a second area AR2 of 0.002 mm². In another preferred embodiment, the first segments 1 have a diameter of 0.2 mm. The second segments have a diameter of 0.03 mm. Further the first segments 1 e.g., have a length L1 that is about 2 mm and the second segment/s 2 e.g., a length L2 that is about 1 mm.

Figure 1C:
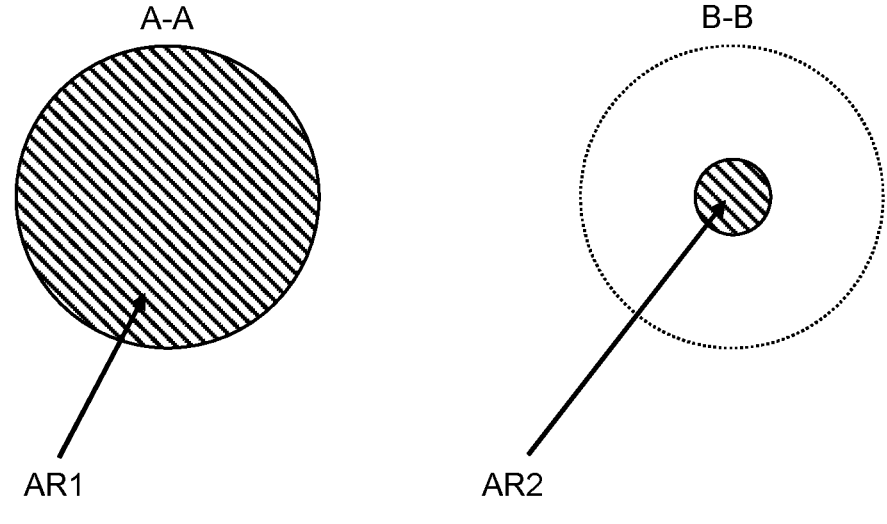

FIG. 1C shows section views of cross sections A-A, B-B of the prior art reference positioning marker 5. As mentioned above, the marker 5 typically comprises a plurality of first segments 1 having a first cross-section A-A and at least one or a plurality of second segments 2 having a second set of cross-sections. The first area AR1 of the first cross-section A-A is selected relatively larger than second area/s AR2 of the second set of cross-sections.

Figure 2A:
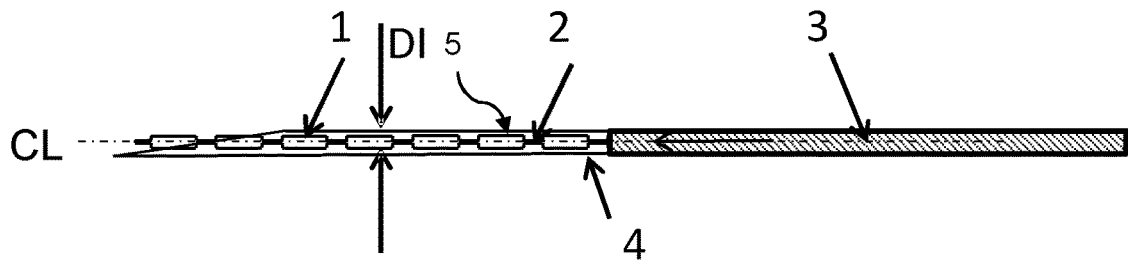
FIG. 2A illustrates a reference positioning marker before implanting into tissue.

FIG. 2A illustrates a reference positioning marker 5 before implanting into tissue. The reference positioning marker 5 is positioned inside a hollow injection needle 4 and ready for implementation in tissue of a patient. The marker 5 comprises an elongated object with a longitudinal axis CL. The elongated object comprises a plurality of first segments 1 having a first cross-section A-A and one or a plurality of second segments 2 having a second set of cross-sections B-B. An area of the first cross-section A-A is selected relatively larger than area/s of the second set of cross-sections B-B. The first segments 1 and the second segments 2 are arranged alternately after each other along the longitudinal axis CL. The longitudinal axis CL of the marker 5 corresponds essentially to a longitudinal axis of the hollow injection needle 4, when the marker 5 is positioned inside the needle 4 before implantation into tissue. A mandrel 3 is arranged to push the marker, in the direction of the arrow.

Figure 2B:
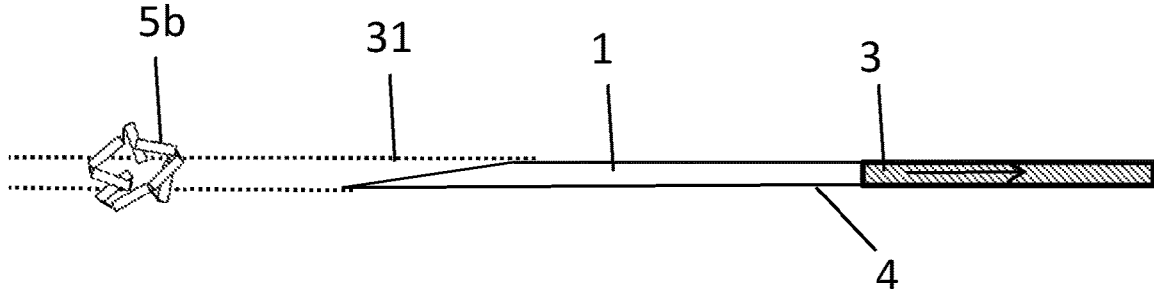
FIG. 2B illustrates a reference positioning marker after being implanted into tissue.

FIG. 2B illustrates a reference positioning marker 5 after being implanted into tissue. The reference positioning marker 5 is shown after implementation in tissue of a patient. As mentioned above, the marker 5 comprises multiple first segments 1 and one or more second segments 2, which, when pushed out of the hollow injection needle 4 by the mandrel 3, folds or crumples, at the second segment/s, into a three-dimensional structure that has a larger diameter/cross section area than the needle 4 and resulting tissue channel 31, or at least a larger diameter/cross section area than the initial cross section area of the marker 5. In other words, the marker 5 forms an entangled and expanding ball 5b of first 1 and second 2 segments when implanted in tissue by exiting the tip of the needle 4.

The marker 5 has the advantage of lodging itself securely into the tissue, as it will expand and have a larger diameter than a tissue channel 31 formed by the hollow injection needle 4, after forming the entangled and expanding ball 5b. This has the advantage of minimizing the risk of the marker 5 changing position over time. This further has the advantage that relatively thin needles can be used leaving a thinner tissue channel as the marker may be of considerably smaller diameter when unfolded, and expand at implementation and therefore be clearly visible in an MRI, X-ray or CT images when in a folded state. In other words, a foldable marker 5 may thus be implanted using a considerably smaller diameter needle 4, which minimizes trauma to the patient, and may be performed even without general anesthesia. The time between marker placement and radiotherapy may consequently be lessened of even omitted.

Figure 3A:
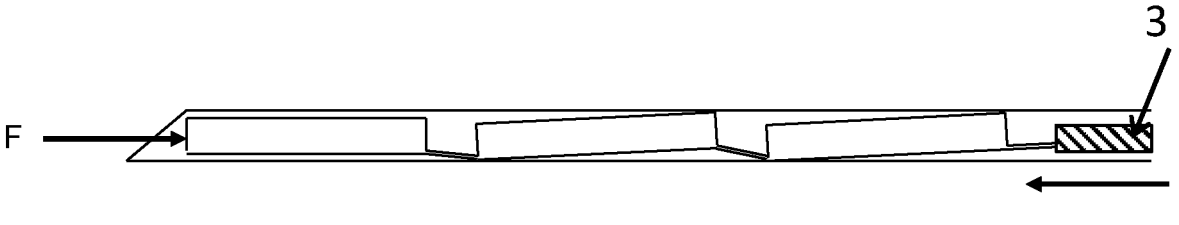
FIG. 3A illustrates unwanted deformation of the prior art reference positioning marker.

FIG. 3A illustrates unwanted deformation of the prior art reference positioning marker 5. When the marker 5 is pushed out of the needle 4 by the mandrel 3, the tissue and/or bending resistance of the second segments will result in a force F acting in the opposite direction to a force exerted by the mandrel 3 trying to push the marker out of the tip of the needle 4.

If the force F exceeds a particular limit, the marker will deform and the first 1 and second 2 segments will no longer remain linearly aligned in the injection needle 4 when it encounters resistance/force F during implantation into the tissue. This will result in increased friction between the marker 5 and the inside of the needle 4, or even cause a complete jam resulting in the marker getting stuck inside the needle 4.

Figure 3B:
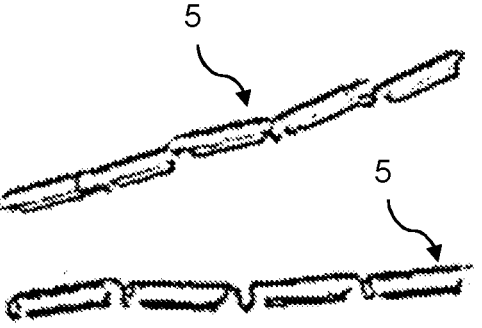
FIG. 3B illustrates further examples of unwanted deformation of the prior art reference positioning marker.

FIG. 3B illustrates examples of unwanted deformation of the prior art reference positioning marker 5. It is understood that any deformation such that he first 1 and second 2 segments no longer remain linearly aligned in the injection needle 4 may occur.

The inventor has addressed this problem in the solution disclosed below. The inventor has developed the prior art reference positioning marker 5 disclosed in FIG. 1A-FIG. 3B into an improved reference positioning marker 5 disclosed below.

Figure 4A:
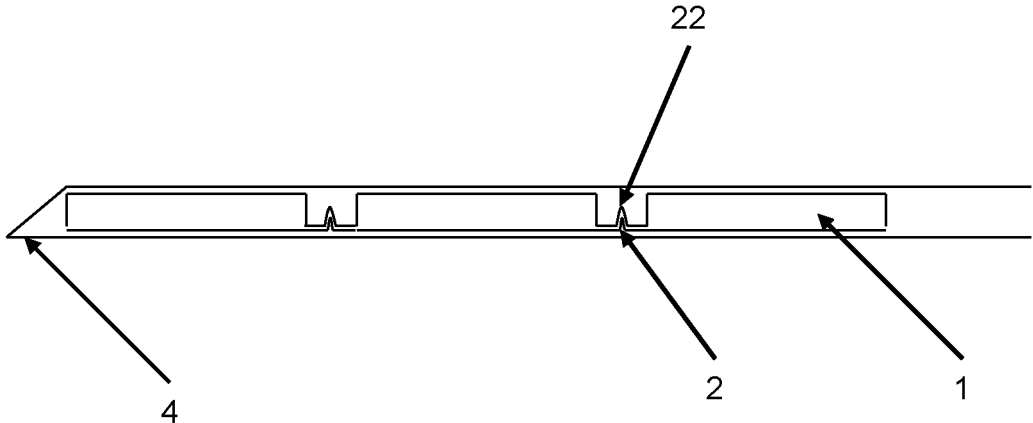
FIG. 4A-B illustrates the inventive concept of a reference positioning marker 5 according to one or more embodiments according to the present disclosure.
Figure 4B:
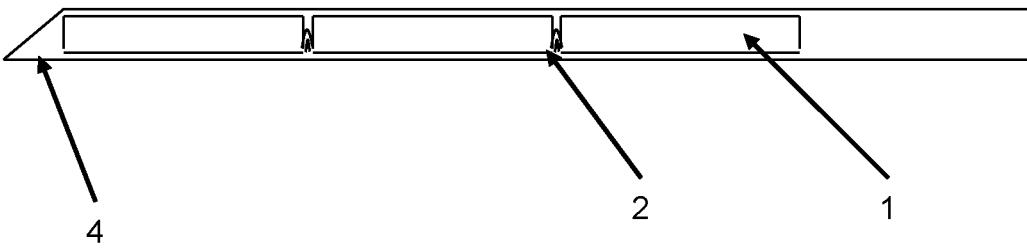

FIG. 4A-B illustrates the inventive concept of a reference positioning marker 5 according to one or more embodiments according to the present disclosure. In FIG. 4A the improved reference positioning marker 5 before deformation and positioned in the needle 4 is shown.

The one or more second segment/s provided with one or more deformation segment/s 22 that ensure that any deformation of the one or more second segments, when positioned inside the needle, occurs in a predetermined location/s between adjoining first segments, such that the plurality of first segments remain linearly aligned in the injection needle when it encounters resistance during implantation into the tissue. In FIG. 4B the improved reference positioning marker 5 after deformation and positioned in the needle 4 is shown.

The reference positioning marker 5 presented herein may be used in radiation therapy and/or microwave therapy and/or cryosurgery and/or ultrasound therapy.

Figure 5A:
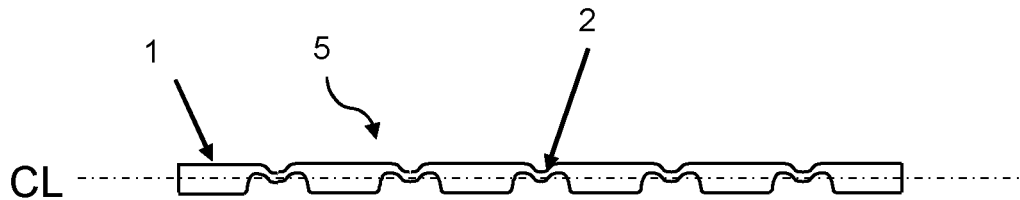
FIG. 5A-B shows side views of a reference positioning marker according to one or more embodiments of the present disclosure.

FIG. 5A shows an overview side view of a reference positioning marker 5 according to one or more embodiments of the present disclosure. The improved reference positioning marker 5 comprises an elongated object with a longitudinal axis CL. The elongated object comprises a plurality of first segments 1 having and one or a plurality of second segments 2. It is understood that a minimal configuration of the marker 5 comprises two first segments and one second segment 2. The first segments 1 and the second segment/s 2 are arranged alternately after each other along the longitudinal axis CL. Any suitable number of first and second segments may be comprised by the elongated object of the marker 5. When positioned in the hollow injection needle 4 (not shown), the longitudinal axis CL of the marker 5 corresponds essentially to a longitudinal axis of the hollow injection needle 4.

Figure 5B:
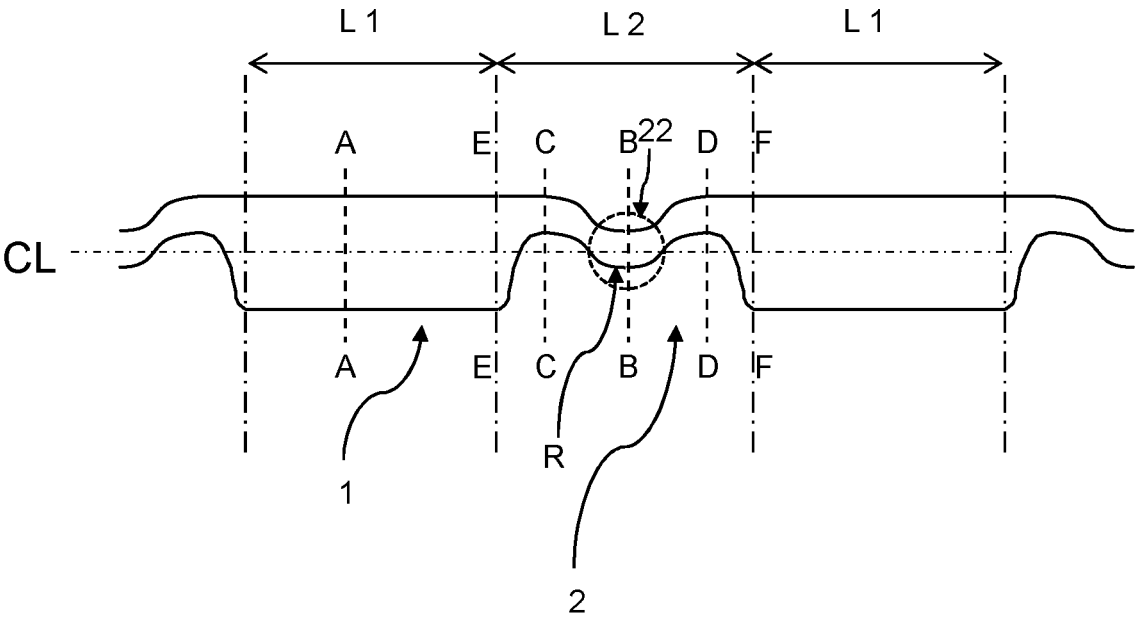

FIG. 5B shows a detailed side view of a reference positioning marker 5 according to one or more embodiments of the present disclosure. The vertical dash-dotted lines mark sections between the first segments 1 and the second segment/s 2. The first segments may e.g., have a first length L1, e.g., about 2 mm, and the second segment/s 2 have. a second length L2, e.g., about 1 mm.

In one example, the first segments have a first length L1 of 1.2 mm and the second segment/s 2 have. a second length L2 of 0.8 mm.

Each of the plurality of first segments 1 have typically a substantially uniform first cross-section A-A, e.g., shaped like a circle, oval, triangle or star. The one or more second segment/s 2 have a second set of cross-sections B-B, C-C, D-D, E-E, F-F. An area of the first cross-section is typically selected relatively larger than area/s of the second set of cross-sections, thereby ensuring that deformation/folding/creasing of the marker 5 occurs in the one or more second segment/s 2.

In other words, by ensuring that at least some of the areas of the second set of cross-sections B-B, C-C, D-D are relatively smaller than the first cross-section A-A, the marker 5 will, when subjected to forces substantially along the longitudinal axis CL, deform/fold/crease at points with least bending resistance of the one or more second segment/s 2.

In one embodiment, a radiation therapy reference positioning marker 5 adapted to be implanted in tissue using a hollow injection needle 4 is provided. The reference positioning marker 5 comprises an elongated object with a longitudinal axis CL and have cross-sections A-A, B-B, C-C, D-D, E-E, F-F of the object, perpendicular to said longitudinal axis (CL), being adapted to fit within an inner diameter DI of the needle 4. The marker 5 is configured to form an entangled and expanding ball 5b of first 1 and second 2 segments when implanted in tissue by exiting the needle (4). Further, the marker 5 comprises a plurality of first segments 1 having a first cross-section A-A and one or more of second segments 2 having a second set of cross-sections B-B, C-C, D-D, E-E, F-F. Further, an area of the first cross-section A-A is selected relatively larger than area/s of the second set of cross-sections B-B, C-C, D-D, E-E, F-F. Further, the first segments 1 and second segment/s 2 are arranged alternately after each other along the longitudinal axis CL. In this embodiment, the one or more second segments 2 are provided with one or more deformation segments 22 adapted to ensure that any deformation of the plurality of second segments, when positioned inside the needle, occurs in a predetermined location/s between adjoining first segments, such that the plurality of first segments remain linearly aligned in the injection needle when it encounters resistance during implantation into the tissue.

As mentioned above, by ensuring that the areas of the second set of cross-sections B-B, C-C, D-D, E-E, F-F are relatively smaller than the first cross-section A-A, the marker 5 will, when subjected to forces substantially along the longitudinal axis CL, deform/fold/crease at points with least bending resistance of the one or more second segment/s 2, i.e., at the deformation segments 22.

Figure 6A:
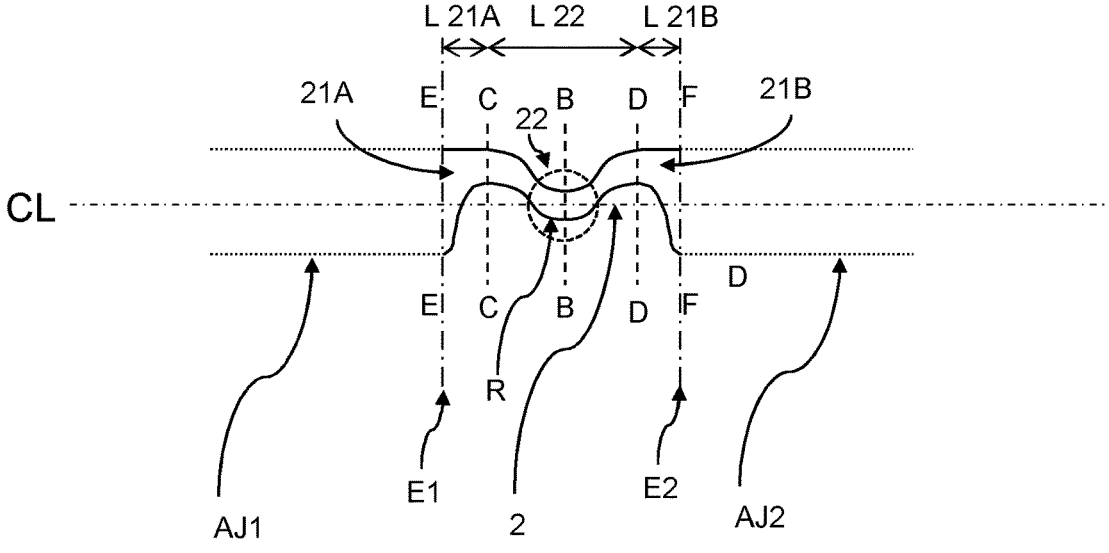
FIG. 6A-B shows a deformation segment formed as a bend according to one or more embodiments of the present disclosure.

FIG. 6A shows a detailed side view of a deformation segment 22 formed as a bend according to one or more embodiments of the present disclosure. In one embodiment, the one or more deformation segments comprises one single deformation segment. In one embodiment, the deformation segment 22 is centered between the respective adjoining first segments AJ1, AJ2 and comprises a minimum area AR2 at a section B-B of the areas AR2, AR3, AR4, AR5, AR6 of the second set of cross-sections B-B, C-C, D-D, E-E, F-F.

In one embodiment, the minimum area AR2 at the section B-B is centered between the respective adjoining first segments AJ1, AJ2. Alternatively, or additionally, the minimum area AR2 is centered around the longitudinal axis CL. In other words, the geometric center/center of mass of the area AR2 at the section B-B is intersected by the longitudinal axis CL.

These embodiments have the advantage that any deformation of the plurality of second segments, when positioned inside the needle, occurs in the middle between adjoining first segments AJ1, AJ2, such that the plurality of first segments remain linearly aligned in the injection needle when it encounters resistance during implantation into the tissue.

In one embodiment, the one or more deformation segments are formed as a bend extending from an outer surface of ends E1, E2 of the respective second segment in a direction towards said longitudinal axis CL.

In one embodiment, the bend has a bending radius R equal to or greater than half of a diameter of a circle CK enclosing an outline of the first cross-section A-A.

In one embodiment, each of the plurality of second segments 2 further comprises two anchor segments 21A-B arranged between either adjoining first segment AJ1, AJ2 respectively and the one or more deformation segments 22. I.e., a first anchor segment 21A is shown between section E-E and section C-C and a second anchor segment 21B is shown between section D-D and section F-F. The first anchor segment 21A has a length L21A along the longitudinal axis CL. The second anchor segment 21B has a length L21B along the longitudinal axis CL.

In one example, the length L21A of the first anchor segment 21A is equal to the length 21B second anchor segment 21B and is in the range of 0.10 to 0.12 mm.

Figure 6B:
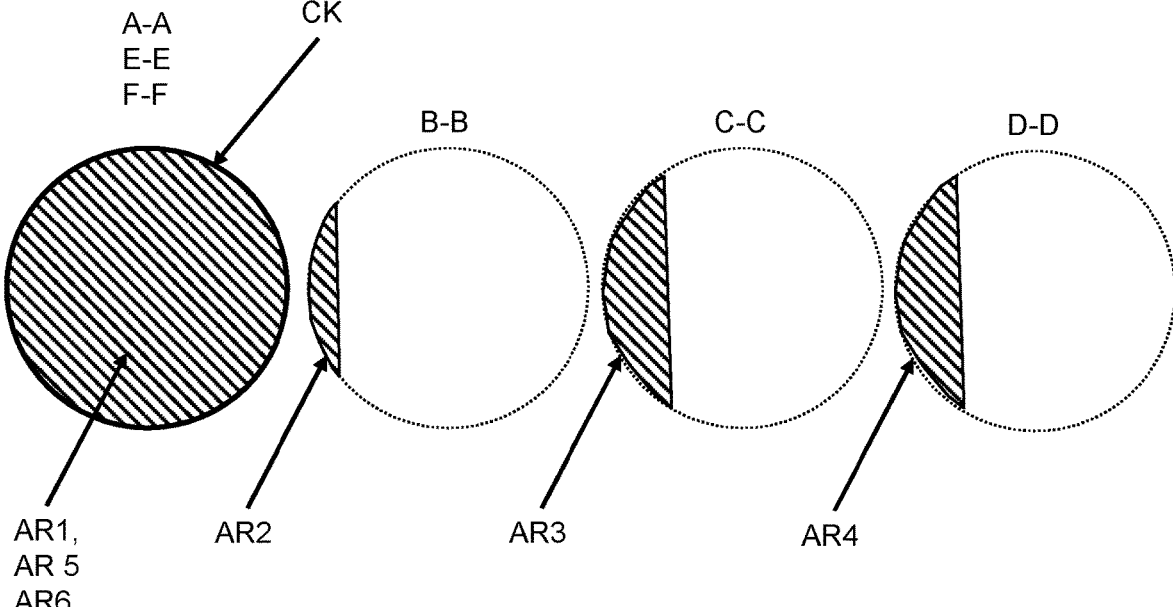

FIG. 6B shows exemplary second set of cross-sections of a second segment according to one or more embodiments of the present disclosure. As can be seen the second segment 2 joins the leftmost adjoining first segments AJ1 at section E-E at a first end E1 (a leftmost end in the figure) and joins the rightmost adjoining first segments AJ2 at section F-F at a second end E2 (a rightmost end in the figure). The minimum area AR2 at a section B-B is centered between the respective adjoining first segments AJ1, AJ2.

A third section C-C made between section E-E and section B-B has a third area AR3 which is relatively smaller than the first area AR1 of the first cross-section A-A and relatively larger than the section B-B centered between the respective adjoining first segments AJ1, AJ2.

A fourth section D-D made between section F-F and section B-B has a fourth area AR4 which is relatively smaller than the first area AR1 of the first cross-section A-A and relatively larger than the section B-B centered between the respective adjoining first segments AJ1, AJ2.

This has the advantage that any deformation of the plurality of second segments, when positioned inside the needle, occurs at section B-B in the middle between adjoining first segments AJ1, AJ2, such that the plurality of first segments remain linearly aligned in the injection needle when it encounters resistance during implantation into the tissue.

In the examples shown in FIG. 6B, the second set of cross-sections B-B, C-C, D-D, E-E, F-F of a second segment are shown as sections of a circle, and the first cross-section A-A is shown as a circle. It is understood that the first segments 1 may have any suitable uniform first cross-section A-A, e.g., shaped like a circle, oval, triangle or star. Similarly, the second set of cross-sections B-B, C-C, D-D, E-E, F-F may be sections of the suitable uniform first cross-section A-A, i.e., sections of a circle, an oval, a triangle or a star.

Figure 7A:
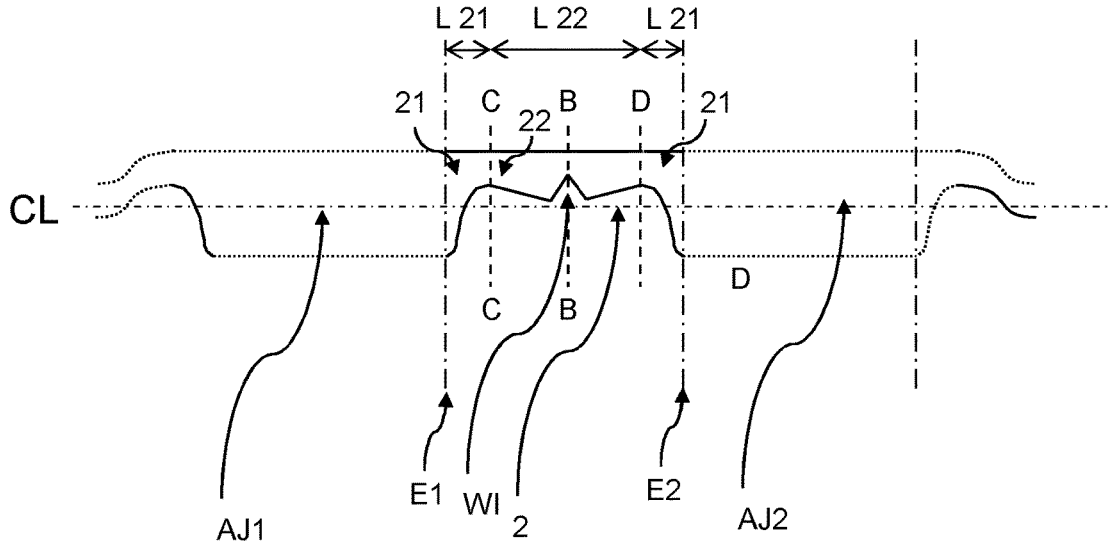
FIG. 7A-B shows a deformation segment comprising a weakening indentation according to one or more embodiments of the present disclosure.

FIG. 7A shows a detailed side view of a deformation segment 22 comprising a weakening indentation WI according to one or more embodiments of the present disclosure. In one embodiment, the one or more deformation segments comprises one single deformation segment. In one embodiment, each of the one or more deformation segments is formed as an elongated element provided with a weakening indentation WI on a side of the deformation segments facing said longitudinal axis CL. The weakening indentation WI is typically centered between the respective adjoining first segments AJ1, AJ2.

This has the effect, that when the deformation segment 22 comprising the weakening indentation WI is subjected to forces along the longitudinal axis CL and is still positioned in the needle 4, the deformation segment 22 will fold at the weakening indentation WI and ensure that the plurality of first segments remain linearly aligned in the injection needle when it encounters resistance during implantation into the tissue.

In one embodiment, each of the plurality of second segments 2 further comprises two anchor segments 21 arranged between either adjoining first segment AJ1, AJ2 respectively and the one or more deformation segments 22. I.e., a first anchor segment 21A is shown between section E-E and section C-C and a second anchor segment 21B is shown between section D-D and section F-F. The first anchor segment 21A has a length L21A along the longitudinal axis CL. The second anchor segment 21B has a length L21B along the longitudinal axis CL.

In one example, the length L21A of the first anchor segment 21A is equal to the length 21B second anchor segment 21B and is in the range of 0.10 to 0.12 mm.

Figure 7B:
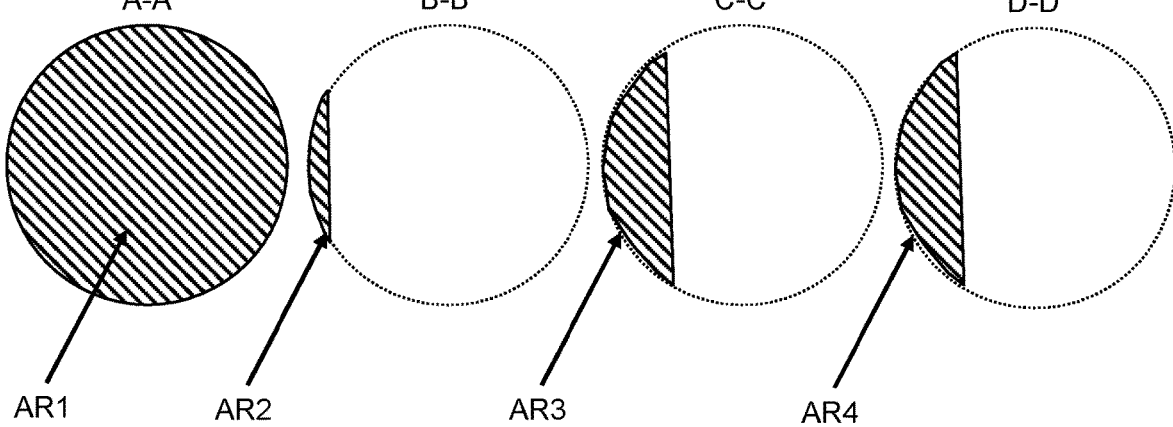

FIG. 7B shows exemplary second set of cross-sections of a second segment according to one or more embodiments of the present disclosure. The areas of the second set of cross-sections of the second segment is further described in relation to FIG. 6B.

Figure 8A:
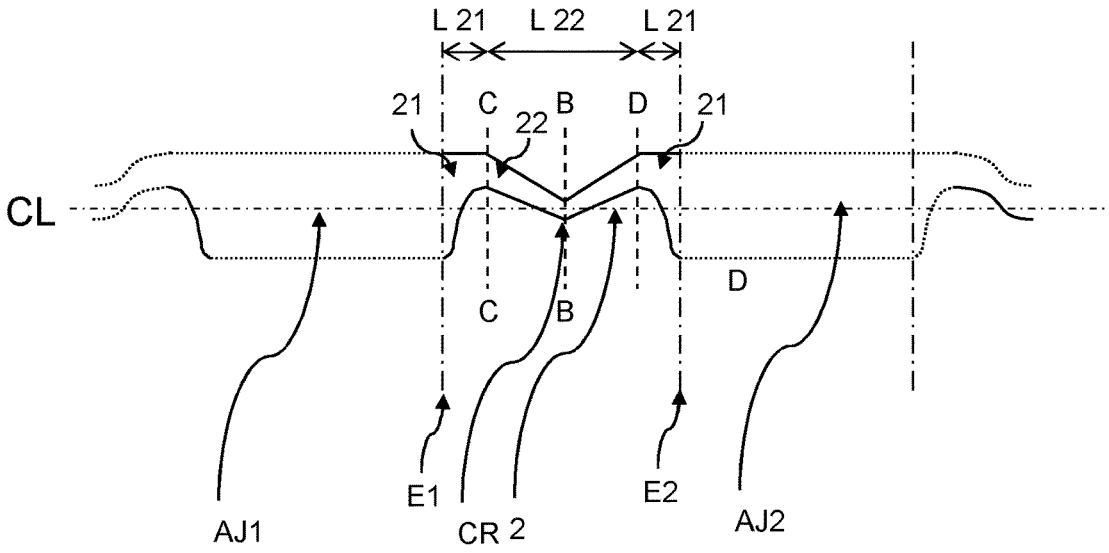
FIG. 8A-B shows a detailed side view of a deformation segment 22 comprising a sharp crease CR according to one or more embodiments of the present disclosure.

FIG. 8A shows a detailed side view of a deformation segment 22 comprising a sharp crease CR according to one or more embodiments of the present disclosure. In one embodiment, the one or more deformation segments comprises one single deformation segment 22. In one embodiment, each of the one or more deformation segments is formed as an elongated element provided with sharp crease, wherein the crease has a direction perpendicular from a cylinder formed by outer surfaces of the first segments towards said longitudinal axis (CL).

In one embodiment, each of the plurality of second segments 2 further comprises two anchor segments 21 arranged between either adjoining first segment AJ1, AJ2 respectively and the one or more deformation segments 22. I.e., a first anchor segment 21A is shown between section E-E and section C-C and a second anchor segment 21B is shown between section D-D and section F-F. The first anchor segment 21A has a length L21A along the longitudinal axis CL. The second anchor segment 21B has a length L21B along the longitudinal axis CL.

Figure 8B:
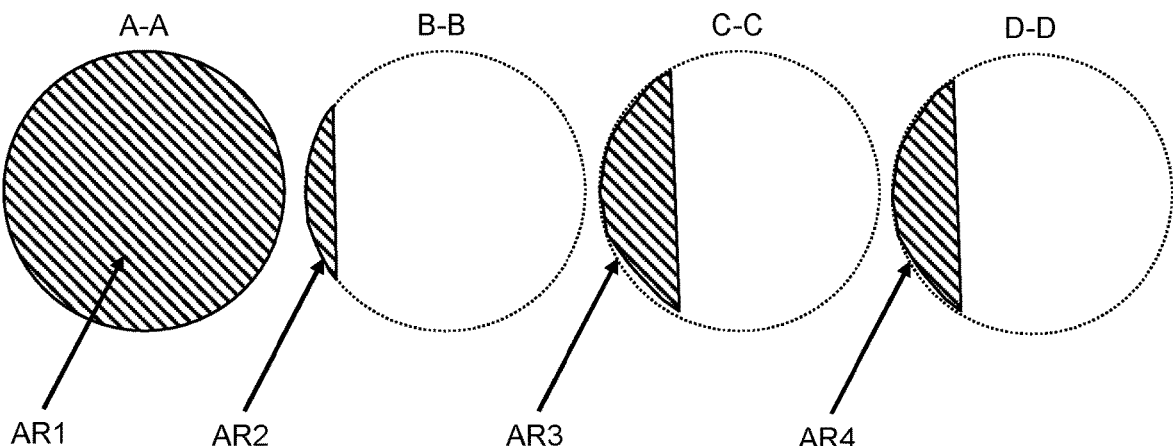

FIG. 8B shows exemplary second set of cross-sections of a second segment according to one or more embodiments of the present disclosure. The areas of the second set of cross-sections of the second segment is further described in relation to FIG. 6B.

FIG. 9A shows a first segment 1 having a circular cross-section according to one or more embodiments of the present disclosure.

Figure 9B:
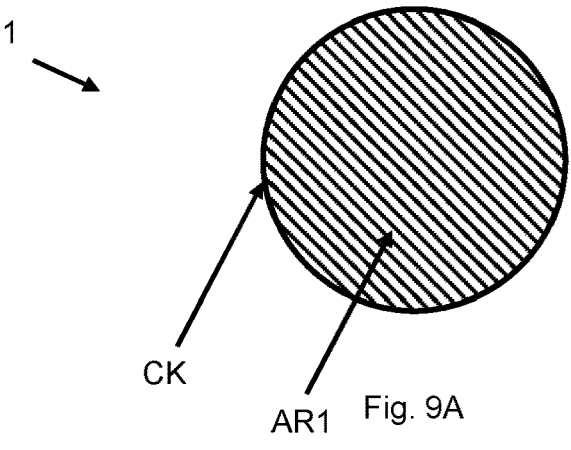
Figure 9B:
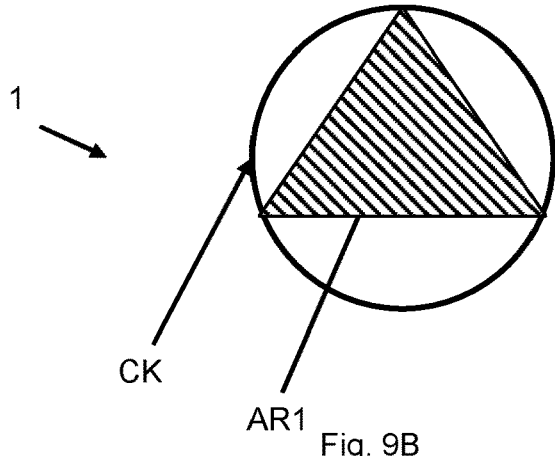

FIG. 9B shows a first segment 1 having a triangular cross-section according to one or more embodiments of the present disclosure.

Figure 9C:
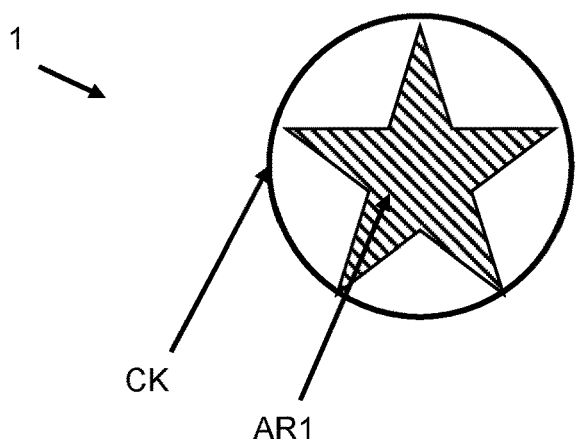

FIG. 9C shows a first segment 1 having a star shaped cross-section according to one or more embodiments of the present disclosure.

Sometimes the initial positioning of the reference positioning marker 5 in tissue of the patient is performed using ultrasound imaging equipment. Depending on the equipment used and the location of the reference positioning marker 5 in the tissue, the visibility of the reference positioning marker 5 in the ultrasound image is reduced. The present disclosure improves the visibility of the reference positioning marker 5 in an ultrasound image by providing reflector elements, e.g., dimples provided with concave face for reflection and focusing ultrasound waves or signals generated by the ultrasound imaging equipment.

Figure 10A:
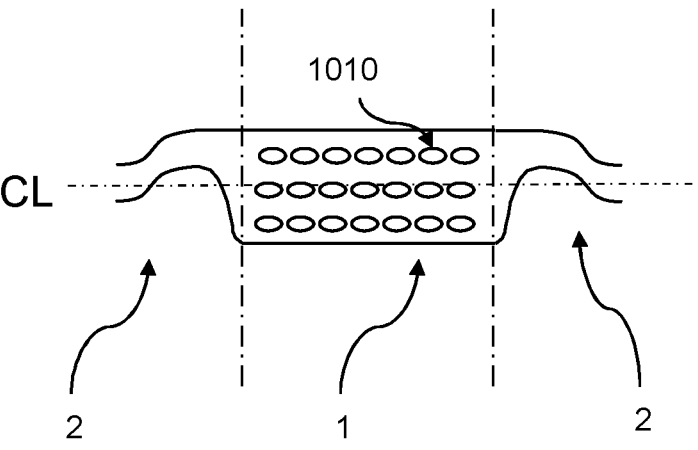
FIG. 10A-B shows a first segment of a reference positioning marker being provided with reflector elements according to one or more embodiments of the present disclosure.

FIG. 10A shows a first segment of a reference positioning marker 5 being provided with reflector elements 1010 according to one or more embodiments of the present disclosure. The vertical dash-dotted lines mark sections between the first segments 1 and the second segment/s 2.

As can be seen in FIG. 10A, the first segment 1 is provided with a plurality of reflector elements 1010, shown as dimples provided with concave face for reflection and focusing ultrasound waves or signals generated by the ultrasound imaging equipment.

Any other recess or indentation, configured to reflect and focus ultrasound waves and/or radiation waves, may be used without departing from the present concept.

Figure 10B:
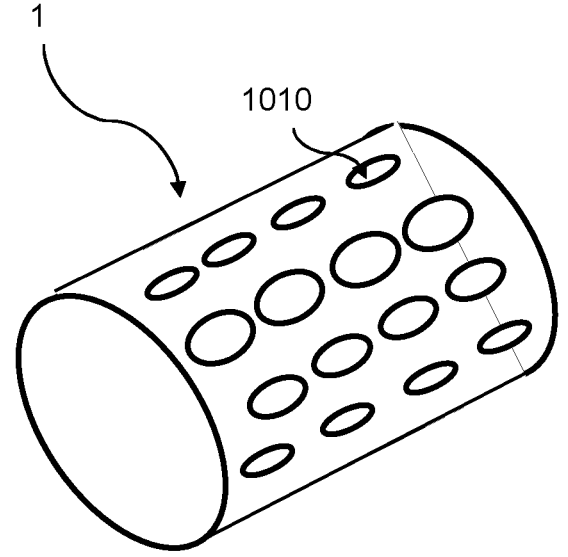

FIG. 10B shows a detailed view of the reference positioning marker 5 being provided with a plurality of reflector elements 1010 according to one or more embodiments of the present disclosure.

The plurality of reflector elements 1010 may in some embodiments be substantially uniformly distributed over the surface of the first segment of the reference positioning marker 5.

The plurality of reflector elements 1010 may in some embodiments comprise indentations, in particular indentations generated by embossing the outer surface of the first segment of the reference positioning marker 5, thereby generating indentations in the outer surface of the first segment of the reference positioning marker 5. The reflector elements 1010 improve visibility when imaging the reference positioning marker 5.

Finally, it should be understood that the invention is not limited to the embodiments described above, but also relates to and incorporates all embodiments within the scope of the appended independent claims.

The invention claimed is:

1. A radiation therapy or microwave therapy or cryosurgery or ultrasound therapy reference positioning marker adapted to be implanted in tissue using a hollow injection needle, wherein the marker comprises an elongated object with a longitudinal axis coinciding with an X-axis in an XYZ orthogonal coordinate system, wherein YZ plane cross-sections of the object are perpendicular to said longitudinal axis, being adapted to fit within an inner diameter of the needle, wherein the marker comprises a plurality of first segments having a first cross-section and one or more second segments having a second set of cross-sections, wherein an area of the first cross-section is selected relatively larger than areas of the second set of cross-sections, and wherein the first segments and second segments are arranged alternately after each other along the longitudinal axis, wherein the one or more of second segments are provided with one or more deformation segments adapted to deform in one or more predetermined locations between adjoining first segments, such that the plurality of first segments remain aligned along the longitudinal axis in the injection needle when the marker encounters resistance during implantation into the tissue, wherein the one or more deformation segments are formed as a bend extending from an outer surface of ends of a respective second segment in a direction towards said longitudinal axis, wherein the bend is non-symmetrical along the longitudinal axis, wherein, in a side view of the one or more deformation segments, an outer surface of the bend defines a concave portion on a first side extending towards said longitudinal axis and a convex portion on a second side that is opposite the first side, each of the concave portion and the convex portion varying in radial distance from the longitudinal axis and having a single apex in said side view, and wherein the respective apexes of the concave portion and the convex portion are coincident and lie in a single YZ plane that is perpendicular to the longitudinal axis, wherein the one or more second segments further comprise first and second anchor segments arranged on opposite sides of the one or more deformation segments, wherein the first anchor segment is arranged between one first adjoining segment and the one or more deformation segments of an adjacent second segment and the second anchor segment is arranged between another first adjoining segment and the one or more deformation segments of the adjacent second segment, wherein the first cross-section is solid, and wherein the second set of cross-sections includes first and second anchor segment cross-sections having respective first and second anchor segment areas, second segment ends cross-sections having respective second segment ends areas, and one or more deformation segment cross-sections having a respective deformation segment area, wherein the first and second anchor segment areas range from being equal to the second segment ends areas of the second segment ends cross-sections to the deformation segment area of the respective one or more deformation segment cross-sections.

2. The marker according to claim 1, wherein the one or more deformation segments are centered between the respective adjoining first segments and each of the respective deformation segment areas comprises a minimum area of any of the areas of the second set of cross-sections.

3. The marker according to claim 1, wherein the convex portion of the outer surface of the bend extends in the direction toward the longitudinal axis and further extends past half of a diameter of the first cross-section.

4. The marker according to claim 1, wherein the marker comprises an alloy or granulation mixture comprising a first material and a second material where the first material constitutes at least 90% by volume of the alloy or granulation mixture and the second material constitutes at most 10% by volume of the alloy or granulation mixture.

5. The marker according to claim 1, wherein the marker comprises between two and fifteen first segments and between one and fourteen second segments.

6. The marker according to claim 1 wherein the marker comprises a plurality of reflector elements.

7. The marker according to claim 2, wherein the minimum area is further centered around the longitudinal axis.

8. The marker according to claim 6, wherein the plurality of reflector elements comprises indentations in the outer surface of the first segments of the reference positioning marker.

* * * * *